(12) United States Patent
Husbands et al.

(10) Patent No.: US 6,559,169 B2
(45) Date of Patent: May 6, 2003

(54) ANTIDEPRESSANT AZAHETEROCYCLYMETHYL DERIVATIVES OF 2,3-DIHYDRO-1,4-BENZODIOXAN

(75) Inventors: George E. M. Husbands, Berwyn, PA (US); Gary P. Stack, Ambler, PA (US); Richard E. Mewshaw, King of Prussia, PA (US); Ian A. Cliffe, Farnham Common (GB)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/128,447

(22) Filed: Apr. 23, 2002

(65) Prior Publication Data
US 2002/0193400 A1 Dec. 19, 2002

Related U.S. Application Data
(60) Provisional application No. 60/286,056, filed on Apr. 24, 2001.

(51) Int. Cl.[7] ............... C07D 401/04; A61K 31/4439
(52) U.S. Cl. .................. 514/338; 514/321; 514/300; 546/277.4; 546/197; 546/113
(58) Field of Search .................. 546/277.4, 197, 546/113; 514/338, 321, 300

(56) References Cited

U.S. PATENT DOCUMENTS

| | | |
|---|---|---|
| 5,242,925 A | 9/1993 | Boettcher et al. |
| 5,371,094 A | 12/1994 | Heine et al. |
| 5,468,767 A | 11/1995 | Cipollina et al. |
| 5,741,789 A | 4/1998 | Hibschman et al. |
| 5,750,724 A | 5/1998 | Kang et al. |
| 5,869,490 A | 2/1999 | Stack |
| 6,458,802 B1 * | 10/2002 | Tran ............... 514/291 |

FOREIGN PATENT DOCUMENTS

| | | |
|---|---|---|
| EP | 0 376 607 A1 | 7/1990 |
| EP | 1 092 715 A2 | 4/2001 |
| WO | WO 98/29415 | 7/1998 |
| WO | WO 98/40386 | 9/1998 |
| WO | WO 99/55695 | 11/1999 |
| WO | WO 00/15636 | 3/2000 |
| WO | WO 01/14330 A2 | 3/2001 |
| WO | WO 02/072587 A1 | 9/2002 |

OTHER PUBLICATIONS

CA 130:168383,Stack 1999.*
CA 128:308493, Stack, 1998.*

* cited by examiner

Primary Examiner—Jane Fan
(74) Attorney, Agent, or Firm—Rebecca R. Barrett

(57) ABSTRACT

Compounds of the formula

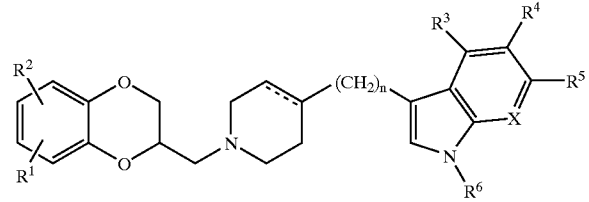

useful for the treatment of depression and other conditions such as obsessive compulsive disorder, panic attacks, generalized anxiety disorder, sexual dysfunction, eating disorders, addictive disorders caused by ethanol or cocaine abuse and related illnesses.

29 Claims, No Drawings

ANTIDEPRESSANT AZAHETEROCYCLYMETHYL DERIVATIVES OF 2,3-DIHYDRO-1,4-BENZODIOXAN

This application claims priority from co-pending provisional application serial No. 60/286,056, filed on Apr. 24, 2001, the entire disclosure of which is hereby incorporated by reference.

BACKGROUND OF THE INVENTION

Major depression is a serious health problem affecting more than 5% of the population, with a life-time prevalence of 15–20%.

Selective serotonin reuptake inhibitors have produced significant success in treating depression and related illnesses and have become among the most prescribed drugs. They nonetheless have a slow onset of action, often taking several weeks to produce their full therapeutic effect. Furthermore, they are effective in fewer than two-thirds of patients.

Serotonin selective reuptake inhibitors (SSRIs) are well known for the treatment of depression and other conditions. SSRIs work by blocking the neuronal reuptake of serotonin, thereby increasing the concentration of serotonin in the synaptic space, and thus increasing the activation of postsynaptic serotonin receptors.

However, although a single dose of an SSRI can inhibit the neuronal serotonin transporter which would be expected to increase synaptic serotonin, long-term treatment is required before clinical improvement is achieved.

It has been suggested that the SSRIs increase the serotonin levels in the vicinity of the serotonergic cell bodies and that the excess serotonin activates somatodendritic autoreceptors, $5HT_{1A}$ receptors, causing a decrease in serotonin release in major forebrain areas. This negative feedback limits the increment of synaptic serotonin that can be induced by antidepressants.

A $5HT_{1A}$ antagonist would limit the negative feedback and should improve the efficacy of the serotonin reuptake mechanism. (Perez, V., et al., *The Lancet*, 349:1594–1597 (1997)). Such a combination therapy would be expected to speed up the effect of the serotonin reuptake inhibitor.

Thus, it is highly desirable to provide improved compounds which both inhibit serotonin reuptake and which are antagonists of the $5HT_{1A}$ receptor.

DESCRIPTION OF THE INVENTION

In accordance with this invention, there is provided a group of novel compounds of the formula:

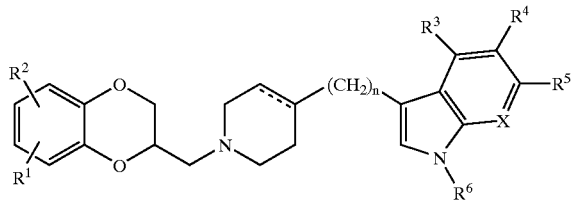

I wherein $R^1$ and $R^2$ are, independently, hydrogen, halogen, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; or $R^1$ and $R^2$, taken together, form methylenedioxy, ethylenedioxy or propylenedioxy;

$R^3$, $R^4$, $R^5$ and $R^7$ are independently selected from hydrogen, halogen, cyano, trifluoromethyl, alkyl of 1 to 6 carbon atoms, alkoxy of 1 to 6 carbon atoms, alkanoyloxy of 2 to 6 carbon atoms;

$R^6$ is hydrogen or alkyl of 1 to 6 carbon atoms;

X is $CR^7$ or N;

A dotted line represents an optional double bond; and n is an integer 0, 1 or 2;

or a pharmaceutically acceptable salt thereof.

In some preferred embodiments of the invention $R^1$ is hydrogen, halo, cyano, carboxamido, trifluoromethyl, amino, alkyl of one to six carbon atoms or alkoxy of one to six carbon atoms.

In other preferred embodiments of the invention $R^2$ is hydrogen, halo, cyano, carboxamido, trifluoromethyl, amino, alkyl of one to six carbon atoms or alkoxy of one to six carbon atoms.

In still more preferred embodiments of the invention one of $R^1$ and $R^2$ is hydrogen and the other one of $R^1$ and $R^2$ is hydrogen, amino, alkoxy, halogen, or carboxamido and more preferably is alkoxy of one to six carbon atoms attached to position 8 of the benzodioxan moiety.

$R^3$, $R^4$ and $R^5$ are preferably independently selected from hydrogen, halo, cyano, alkyl of one to six carbon atoms, and alkoxy of one to six carbon atoms in some embodiments of the invention. In more preferred embodiments of the invention $R^3$, $R^4$ and $R^5$ are independently selected from hydrogen, halogen, cyano, and alkoxy.

n is preferably 0 or 1.

The optional double bond is preferably present.

X is preferably $CR^7$. When X is $CR^7$, $R^7$ is preferably hydrogen, halo, cyano, alkyl of one to six carbon atoms or alkoxy of one to six carbon atoms and more preferably hydrogen, halogen, cyano or alkoxy.

Still more preferred are compounds wherein $R^1$ and $R^2$ are, independently, hydrogen, halo, cyano, carboxamido, trifluoromethyl, amino, alkyl of one to six carbon atoms or alkoxy of one to six carbon atoms; $R^3$, $R^4$ and $R^5$ are independently selected from hydrogen, halo, cyano, alkyl of one to six carbon atoms, and alkoxy of one to six carbon atoms; and n is an integer 0 or 1.

Yet more preferred are those compounds in which $R^1$ is alkoxy of one to six carbon atoms and is attached to position 8 of the benzodioxan moiety, $R^2$ and $R^6$ are hydrogen, $R^3$, $R^4$ and $R^5$ are independently selected from hydrogen, halogen and cyano, X is $CR^7$, $R^7$ is hydrogen, halo, cyano, n is 0 and the dotted line represents a double bond.

This invention relates to both the R and S stereoisomers of the 2-aminomethyl-2,3-dihydro-1,4-benzodioxan, as well as to mixtures of the R and S stereoisomers. Throughout this application, the name of the product of this invention, where the absolute configuration of the 2-aminomethyl-2,3-dihydro-1,4-benzodioxan is not indicated, is intended to embrace the individual R and S enantiomers as well as mixtures of the two. In some preferred embodiments of the present invention the S stereoisomer is preferred.

Where a stereoisomer is preferred, it may in some embodiments be provided substantially free of the corresponding enantiomer. Thus, an enantiomer substantially free of the corresponding enantiomer refers to a compound which is isolated or separated via separation techniques or prepared free of the corresponding enantiomer. Substantially free, as used herein means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

Alkyl as used herein refers to an aliphatic hydrocarbon chain and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms.

Alkanamido as used herein refers to the group R—C(=O)—NH— where R is an alkyl group of 1 to 5 carbon atoms.

Alkanoyloxy as used herein refers to the group R—C(=O)—O— where R is an alkyl group of 1 to 5 carbon atoms.

Alkanesulfonamido as used herein refers to the group R—S(O)$_2$—NH— where R is an alkyl group of 1 to 6 carbon atoms.

Alkoxy as used herein refers to the group R—O— where R is an alkyl group of 1 to 6 carbon atoms.

Carboxamido as used herein refers to the group —CO—NH$_2$.

Carboalkoxy as used herein refers to the group R—O—C(=O)— where R is an alkyl group of 1 to 5 carbon atoms.

Halogen (or halo) as used herein refers to chlorine, bromine, fluorine and iodine.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific compounds of the present invention are:
5-methoxy-3-[4-[1,2,3,6-tetrahydro-1-[2-(2,3-dihydro-[1,4]benzodioxinyl)]-methyl]pyridinyl]indole;
5-fluoro-3-[4-[1,2,3,6-tetrahydro-1-[2-(2,3-dihydro[1,4]benzodioxinyl)]methyl]pyridinyl]indole;
3-[4-(1H-indol-3-yl)-3,6-dihydro-2H-pyridin-1-ylmethyl]-2,3-dihydro-benzo[1,4]dioxin-7-ylamine;
2-[4-(1H-indol-3-yl)-3,6-dihydro-2H-pyridin-1-ylmethyl]-2,3-dihydro-benzo[1,4]dioxin-6-ylamine;
3-[1-(8-methoxy-2,3-dihydro-benzo[1,4]dioxin-2-ylmethyl)-1,2,3,6-tetrahydro-pyridin-4-yl]-1H-indole;
2-[4-(5-fluoro-1H-indol-3-yl)-3,6-dihydro-2H-pyridin-1-ylmethyl]-2,3-dihydro-benzo[1,4]dioxin-6-ylamine;
3-[1-(8-methoxy-2,3-dihydro-benzo[1,4]dioxin-2-ylmethyl)-1,2,3,6-tetrahydro-pyridin-4-yl]-1H-indole-5-carbonitrile;
3-[1-(8-methoxy-2,3-dihydro-benzo[1,4]dioxin-2-ylmethyl)-1,2,3,6-tetrahydro-pyridin-4-yl]-1H-pyrrolo[2,3-b]pyridine;
6-fluoro-3-[1-(8-methoxy-2,3-dihydro-1,4-benzodioxin-2-ylmethyl)-1,2,3,6-tetrahydro-pyridin-4-yl]-1H-indole;
3-[4-(1H-indol-3-yl)-3,6-dihydro-2H-pyridin-1-ylmethyl]-2,3-dihydro-benzo[1,4]dioxin-5-carboxylic acid amide;
3-[4-(5-fluoro-1H-indol-3-yl)-3,6-dihydro-2H-pyridin-1-ylmethyl]-2,3-dihydro-benzo[1,4]dioxin-5-carboxylic acid amide;
3-(1-{[8-fluoro-2,3-dihydro-1,4-benzodioxin-2-yl]methyl}-1,2,3,6-tetrahydro-pyridin-4-yl)-1H-indole;
3-(1-{[7-methoxy-2,3-dihydro-1,4-benzodioxin-2-yl]methyl}-1,2,3,6-tetra-hydropyridin-4-yl)-1H-indole; and
5-fluoro-3-[1-(8-methoxy-2,3-dihydro-benzo[1,4]dioxin-2-ylmethyl)-1,2,3,6-tetrahydro-pyridin-4-yl]-1H-indole,
and pharmaceutically acceptable salts thereof.

The compounds of the invention are prepared by conventional methods. Specifically, the appropriate azaheterocycle is combined with a suitably substituted benzodioxan methyltosylate or bromide (II) in a solvent such as dimethyl sulfoxide and heated to a temperature of 70–100° C. for several hours as illustrated in Scheme I below. Alternatively, the azaheterocycle may be acylated with a suitably substituted benzodioxan carboxylic acid chloride, and the resulting amide reduced to the amine with an appropriate reducing agent such as lithium aluminum hydride or borane/THF. The azaheterocycle may also be Scheme I

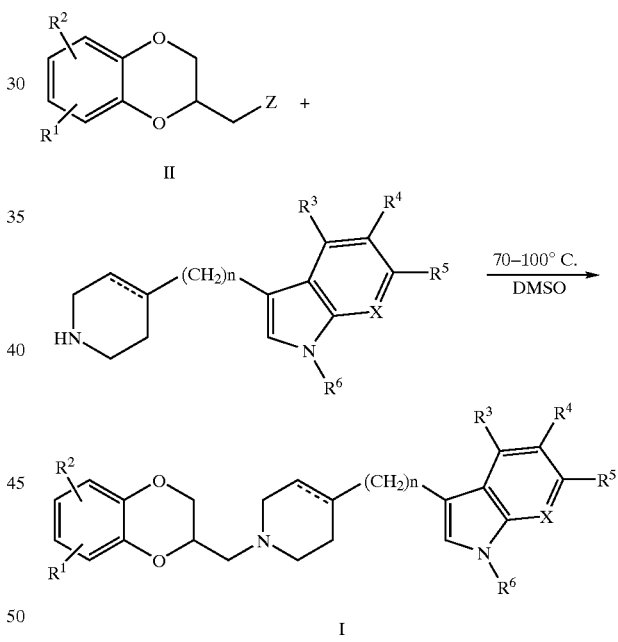

combined with a suitably substituted benzodioxan carboxaldehyde in the presence of a reducing agent such as sodium cyanoborohydride.

The azaheterocycles required to prepare the compounds of the invention are known compounds. The benzodioxan methyltosylates and halides are known compounds or they may be prepared from the appropriately substituted salicylaldehydes by the method (1) described in Scheme II below. The salicylaldehyde (1) is alkylated with an epihalohydrin or glycidyl arylsulfonate in the presence of a suitable base. The aldehyde moiety (2) is then converted to a phenol by a Baeyer-Villager procedure and cyclization to the benzodioxan methanol effected by treatment with a base such as potassium carbonate. The alcohol (3) is elaborated to a tosylate by treatment with p-toluenesulfonyl chloride and a tertiary amine base or to a bromide by treatment with triphenylphosphine and carbon tetrabromide. Alternatively (2), the substituted salicylaldehyde (1) may be protected with a suitable protecting group such as benzyl to produce (4) and the aldehyde converted to a phenol (5) as described above. Following elaboration of the phenol to the glycidyl ether (6) by treatment with an epihalohydrin or glycidyl arylsulfonate, deprotection and cyclization are effected in a single step via a transfer hydrogenation in the presence of sodium bicarbonate. The bromide or tosylate is prepared as described above to produce II. Or the benzodioxan methylbromide Scheme II

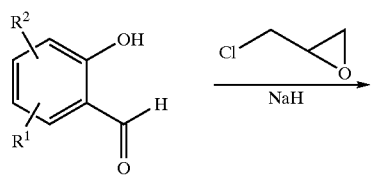

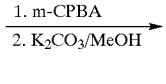

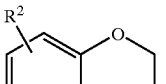

may be prepared from a suitably substituted guaiacol by procedure (3) shown above in Scheme II. The guiacol (7) is alkylated with a glycidyl arylsulfonate or an epihalohydrin as described above to produce (8). The methyl ether is then cleaved by treatment with 48% HBr; this also converts the epoxide to a bromohydrin (9). Cyclization directly to the benzodioxan methylbromide (IIb) is effected by the Mitsonobu procedure.

The compounds of the invention may be resolved into their enantiomers by conventional methods or, preferably, they may be prepared directly by substitution of (2R)-(−)-glycidyl 3-nitrobenzenesulfonate or tosylate (for the S benzodioxan methylamine) or (2S)-(+)-glycidyl 3-nitrobenzenesulfonate or tosylate (for the R enantiomer) in place of epichlorohydrin in the procedure above.

A protocol similar to that used by Cheetham et. al. (Neuropharmacol. 32:737, 1993) was used to determine the affinity of the compounds of the invention for the serotonin transporter. The compound's ability to displace $^3$H-paroxetine from male rat frontal cortical membranes was determined using a Tom Tech filtration device to separate bound from free $^3$H-paroxetine and a Wallac 1205 Beta Plate® counter to quantitate bound radioactivity. $K_i$'s thus determined for standard clinical antidepressants are 1.96 nM for fluoxetine, 14.2 nM for imipramine and 67.6 nM for zimelidine. A strong correlation has been found between $^3$H-paroxetine binding in rat frontal cortex and $^3$H-serotonin uptake inhibition.

High affinity for the serotonin 5-HT$_{1A}$ receptor was established by testing the claimed compound's ability to displace [$^3$H] 8-OHDPAT (dipropylaminotetralin) from the 5-HT$_{1A}$ serotonin receptor following a modification of the procedure of Hall et al., J. Neurochem. 44, 1685 (1985) which utilizes CHO cells stably transfected with human 5-HT$_{1A}$ receptors. The 5-HT$_{1A}$ affinities for the compounds of the invention are reported below as $K_i$'s.

Antagonist activity at 5-HT$_{1A}$ receptors was established by using a $^{35}$S-GTPγS binding assay similar to that used by Lazareno and Birdsall (Br. J. Pharmacol. 109: 1120, 1993), in which the test compound's ability to affect the binding of $^{35}$S-GTPγS to membranes containing cloned human 5-HT$_{1A}$ receptors was determined. Agonists produce an increase in binding whereas antagonists produce no increase but rather reverse the effects of the standard agonist 8-OHDPAT. The test compound's maximum inhibitory effect is represented as the $I_{max}$, while its potency is defined by the IC$_{50}$.

The results of the three standard experimental test procedures described in the preceding three paragraphs were as follows:

| Compound | 5-HT Transporter Affinity KI (nM) | 5-HT$_{1A}$ Receptor Affinity KI (nM) | 5-HT1A Function IC$_{50}$ (nM) (I$_{max}$) |
|---|---|---|---|
| Example 1 |  | 27.18 |  |
| Example 2 | 16.00 | 68.29 |  |
| Example 3 | 1.16 | 30.98 | 232.0 (96.0) |
| Example 4 | 2.03 | 131.55 | 240.0 (90.0) |
| Example 5 | 0.17 | 2.85 | 57.3 (89.3) |
| Example 6 | 0.34 | 46.73 | 411.3 (96.7) |
| Example 7 | 1.04 | 7.95 | 82.5 (100) |
| Example 8 | 39.00 | 4.30 | 26.0 (94.0) |
| Example 9 | 0.60 | 4.88 | 272.0 (80.0) |
| Example 10 | 4.96 | 64.58 | 1279.0 (61.0) |
| Example 11 | 3.13 | 70.57 | 736.0 (60.0) |
| Example 12 | 49.00 | 35.51 | 521.0 (76.0) |
| Example 13 | 40.00 | 17.29 | 522.0 (100) |
| Example 14 | 1.79 | 8.57 | 70.0 (100) |

Like the antidepressants fluoxetine, paroxetine and sertraline, the compounds of this invention have the ability to potently block the reuptake of the brain neurotransmitter serotonin. They are thus useful for the treatment of diseases commonly treated by the administration of serotonin selective reuptake inhibitor (SSRI) antidepressants, such as depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive compulsive disorder (including trichotillomania), social anxiety disorder, generalized anxiety disorder, obesity, eating disorders such as anorexia nervosa, bulimia nervosa, vasomotor flushing, cocaine and alcohol addiction, sexual dysfunction (including premature ejaculation), and related illnesses. Moreover, the compounds of this invention have potent affinity for and antagonist activity at brain 5-HT$_{1A}$ serotonin receptors. Recent clinical trials employing drug mixtures (eg, fluoxetine and pindolol) have demonstrated a more rapid onset of antidepressant efficacy for a treatment combining SSRI activity and 5-HT$_{1A}$ antagonism (Blier and Bergeron, 1995; F. Artigas et. al., 1996; M. B. Tome et. al., 1997). The compounds of the invention are thus exceedingly interesting and useful for treating depressive illnesses.

Thus the present invention provides methods of treating, preventing, inhibiting or alleviating each of the maladies listed above in a mammal, preferably in a human, the methods comprising providing a pharmaceutically effective amount of a compound of this invention to the mammal in need thereof.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in *Remingtons Pharmaceutical Sciences*, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 5 mg per day with gradual increase in the daily dose to about 150 mg per day, to provide the desired dosage level in the human.

Provide as used herein means either directly administering a compound or composition of the present invention, or administering a prodrug, derivative or analog which will form an equivalent amount of the active compound or substance within the body.

The present invention includes prodrugs of compounds of Formula I. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., Journal of Drug Deliver Reviews, 8:1–38(1992), Bundgaard, J. of Pharmaceutical Sciences, 77:285 et seq. (1988); and Higuchi and Stella (eds.) Prodrugs as Novel Drug Delivery Systems, American Chemical Society (1975).

The following examples illustrate the production of representative compounds of this invention.

EXAMPLE 1

5-Methoxy-3-[4-[1,2,3,6-tetrahydro-1-[2-(2,3-dihydro[1,4]benzodioxinyl)]methyl]pyridinyl]indole 2,3-Dihydro-benzo[1,4]dioxin-2-ylmethyl 4-methylbenzenesulfonate (1.10 g, 3.44 mmole) was dissolved in a mixture of dimethylformamide/tetrahydrofuran (1:1 v/v, 30 mL) and 5-methoxy-3-(1,2,3,6-tetrahydro-4-pyridinyl)-1H-indole (0.80 g, 3.5 mmole) added, followed by sodium bicarbonate (1.0 g), and the mixture was refluxed under nitrogen for 18 hours, The solvent was removed under vacuum and the residue partitioned between 400 mL each of methylene chloride and water. The layers were separated and the organic phase was washed with water and saturated sodium chloride solution, dried over magnesium sulfate and evaporated to a foam (0.70 g). A sample was converted to the oxalate salt, m.p. 120° C. (dec.).

Elemental Analysis for: $C_{23}H_{24}N_2O_3 \cdot C_2H_2O_4 \cdot 0.50\ H_2O$

Calc'd: C, 63.15; H, 5.72; N, 5.89

Found: C, 63.04; H, 5.61; N, 5.84

EXAMPLE 2

5-Fluoro-3-[4-[1,2,3,6-tetrahydro-1-[2-(2,3-dihydro[1,4]benzodioxinyl)]methyl]pyridinyl]indole 2,3-Dihydro-benzo[1,4]dioxin-2-ylmethyl 4-methylbenzenesulfonate (1.18 g, 3.5 mmole) was dissolved in a mixture of dimethylformamide/tetrahydrofuran (1:1 v/v, 30 mL) and 5-fluoro-3-(1,2,3,6-tetrahydro-4-pyridinyl)-1H-indole (0.60 g, 2.8 mmole) added, followed by sodium bicarbonate (1.0 g), and the mixture was refluxed under nitrogen for 18 hours. The solvent was evaporated under vacuum, and the residue partitioned between 400 mL each of water and methylene chloride. The layers were separated and the organic phase was washed with water and saturated aqueous sodium chloride solution, dried over magnesium sulfate and filtered. The filtrate was evaporated under vacuum to yield a solid (0.50 mg). A portion of this residue was converted to the oxalate salt, m.p, 145° C. (dec).

Elemental Analysis for: $C_{22}H_{21}FN_2O_2 \cdot C_2H_2O_4 \cdot 0.50\ H_2O$

Calc'd: C, 62.20; H, 5.22; N, 6.04

Found: C, 62.39; H, 5.08; N, 6.06

EXAMPLE 3

3-[4-(1H-Indol-3-yl)-3,6-dihydro-2H-pyridin-1-ylmethyl]-2,3-dihydro-benzo[1,4]dioxin-7-ylamine (2R)-2-(Bromomethyl)-7-nitro-2,3-dihydro-benzo[1,4]dioxin (1.0 g, 3.6 mmole) was dissolved in DMSO (50 mL) and 3-(1,2,3,6)-tetrahydro-4-pyridinyl-1H-indole (0.60 g, 3.0 mmole) added and the mixture was heated under nitrogen at 80° C. for four hours. The reaction mixture was cooled and added to water (100 mL). The mixture was extracted with methylene chloride. The organic layer was washed with water and saturated aqueous sodium chloride solution, dried over anhydrous potassium carbonate, and filtered. The filtrate was evaporated in vacuum to give 1.0 g of the nitro intermediate as an amorphous residue. This was dissolved in methanol and added to a refluxing mixture of hydrazine hydrate (1.25 mL, mmole) and Raney Nickel (1.25 g) in methanol (15 mL) and the reaction mixture was refluxed for 30 minutes. The hot reaction mixture was filtered through celite and the filtrate evaporated in vacuum. The residue was crystallized from isopropanol, giving a light yellow solid, m.p. 204–206° C.

Elemental Analysis for: $C_{22}H_{23}N_3O_2 \cdot 0.25\ H_2O$

Calc'd: C, 72.21; H, 6.47; N, 11.48

Found: C, 72.48; H, 6.38; N, 11.51

EXAMPLE 4

2-[4-(1H-Indol-3-yl)-3,6-dihydro-2H-pyridin-1-ylmethyl]-2,3-dihydro-benzo[1,4]dioxin-6-ylamine (2R)-2-(Bromomethyl)-6-nitro-2,3-dihydro-benzo[1,4]dioxin (1.0 g, 3.6 mmole) was dissolved in DMSO (50 mL) and 3-(1,2,3-6-tetrahydro-H-pyridinyl-1H-indole (0.60 g, 3.0 mmole) added. The solution was heated at 80° C. under nitrogen for 16 hours and then allowed to cool to room temperature and poured into water (100 mL). The product was extracted using methylene chloride (100 mL). This extract was washed with water, and saturated sodium chloride solution, dried over anhydrous potassium carbonate, filtered and evaporated in vacuum, yielding 3-[1-[(2S)-6-nitro-2,3-dihydro-benzo[1,4]dioxo-2-yl)-1,2,3,6-tetrahydropyridin-4-yl]-1H-indole as a yellow solid, m.p. 183–185° C. (1.2 g, 83%).

Elemental Analysis for: $C_{22}H_{21}N_3O_4.0.25\ H_2O$

Calc'd: C, 66.74; H, 5.47; N, 10.61

Found: C, 66.57; H, 5.24; N, 10.37

To a refluxing solution of hydrazine hydrate (1.25 mL, 25 mmole) in methanol (20 mL) containing Raney Nickel (1.25 g) was added a warm methanol solution of 3-[1-(2S)-6-nitro-2,3-dihydro-benzo[1,4]dioxin-2-ylmethyl)-1,2,3,6-tetrahydro-pyridin-4-yl]-1H-indole (1.0 g, 2.6 mmole) under nitrogen. The reaction mixture was refluxed for 45 minutes, during which time all reacting solids dissolved. The reaction mixture was filtered through celite while hot, and the filtrate evaporated in vacuum. The solid obtained was recrystallized from isopropanol to give 200 mg of the (S)-enantiomer of the title compound as a light yellow solid, m.p. 199–200° C.

Elemental Analysis for: $C_{22}H_{23}N_3O_2$

Calc'd: C, 73.11; H, 6.41; N, 11.63

Found: C, 72.82; H, 6.39; N, 11.51

EXAMPLE 5

3-[1-(8-Methoxy-2,3-dihydro-benzo[1,4]dioxin-2-ylmethyl)-1,2,3,6-tetrahydro-pyridin-4-yl]-1H-indole (2R)-8-Methoxy-2,3-dihydro-benzo[1,4]dioxin-2-yl]methyl-4-methylbenzenesulfonate (1.1 g, 3.1 mmole) was dissolved in a mixture of dimethylformamide/tetrahydrofuran (1:1 v/v, 50 mL) and 3-(1,2,3,6-tetrahydro-4-pyridinyl)-1H-indole (0.60 g 1.6 mmole) added, followed by sodium bicarbonate (1.0 g). The reaction mixture was refluxed under nitrogen for 18 hours, then cooled and concentrated in vacuum. The residue was partitioned between 400 mL each of water and ethyl acetate. The layers were separated. The organic phase was washed with water and saturated aqueous sodium chloride solution, dried over anhydrous potassium carbonate and evaporated to a foam (1.0 g). Trituration with ether yielded a solid which was recrystallized from boiling chloroform/methanol (1:1 v/v) to give 0.40 g (40%) of the (S)-enantiomer of the title compound as an off-white solid one-quarter hydrate, m.p. 203–205° C.

Elemental Analysis for: $C_{23}H_{24}N_2O_3.0.25\ H_2O$

Calc'd: C, 72.51; H, 6.48; N, 7.35

Found: C, 72.27; H, 6.34; N, 7.30

EXAMPLE 6

2-[4-(5-Fluoro-1H-indol-3-yl)-3,6-dihydro-2H-pyridin-1-ylmethyl]-2,3-dihydro-benzo[1,4dioxin-6-ylamine (2R)-2-(Bromomethyl)-6-nitro-2,3-dihydro-benzo[1,4]dioxin (2 g, 7.3 mmole) was dissolved in DMSO (50 mL) and 5-fluoro-3-(1,2,3,6-tetrahydro-4-pyridinyl)-1H indole (1.0 g, 4.6 mmole) added. The reaction mixture was heated at 90° C. under nitrogen for 18 hours. The reaction mixture was cooled, poured into water (100 mL) and the product extracted using methylene chloride. The organic phase was washed with water and saturated aqueous sodium chloride solution, dried over anhydrous potassium carbonate and filtered. The filtrate was evaporated in vacuum to give a solid (0.90 g). The solid was added to a refluxing solution of hydrazine hydrate (1.25 mL, 25 mmole) in methanol (20 mL) containing Raney Nickel (1.25 g) under nitrogen. The reaction mixture was refluxed for 45 minutes, during which time the reagents dissolved. The catalyst was removed by filtration through celite and the filtrate evaporated in vacuum. The residue was crystallized from methylene chloride to give 0.30 g of the (S)-enantiomer of the title product as a white solid (m.p. 172–174° C.) containing 0.06 equivalents of methylene chloride.

Elemental Analysis for: $C_{22}H_{22}FN_3O_2.0.06\ CH_2Cl_2$

Calc'd: C, 68.91; H, 5.80; N, 10.93

Found: C, 68.51; H, 5.70; N, 10.70

EXAMPLE 7

3-[1-(8-Methoxy-2,3-dihydro-benzo[1,4]dioxin-2-ylmethyl)-1,2,3,6-tetrahydro-pyridin-4-yl]-1H-indole-5-carbonitrile 3-(1,2,3,6-Tetrahydro-4-pyridinyl)1H-indole-5-carbonitrile (0.70 g, 3.1 mmole) and [(2R)-8-methoxy-2,3-dihydro-benzo[1,4]dioxin-2-ylmethyl-4-methylbenzenesulfonate (040 g, 1.1 mmole) were dissolved in a mixture of dimethylformamide/tetrahydrofuran (1:1 v/v, 50 mL) and sodium bicarbonate (1.0 g) added. The reaction mixture was refluxed under nitrogen for 18 hours. The solvent was evaporated in vacuum and the residue partitioned between 400 mL each of methylene chloride and water. The organic phase was separated, washed with water and saturated aqueous sodium chloride solution, dried over magnesium sulfate and filtered. The filtrate was evaporated in vacuum to give a solid which was purified by column chromatography on silica gel. Elution with 2% methanol in chloroform, concentration of the product fractions in vacuum and treatment of an ethereal solution of the residue with 4 N isopropanolic HCl gave the (S)-enantiomer of the title compound (250 mg, 54% ) as a yellow solid hydrochloride, one-quarter hydrate, m.p. 235–238° C.

Elemental Analysis for: $C_{24}H_{23}N_3O_3.HCl.0.25\ H_2O$

Calc'd: C, 65.15; H, 5.58; N, 9.50

Found: C, 64.96; H, 5.59; N, 9.09

EXAMPLE 8

3-[1-(8-Methoxy-2,3-dihydro-benzo[1,4]dioxin-2-ylmethyl)-1,2,3,6-tetrahydro-pyridin-4-yl]-1H-pyrrolo[2,3-b]pyridine

[(2R)-8-Methoxy-2,3-dihydro-benzo[1,4]dioxin-2-yl]methyl 4-methylbenzenesulfonate (0.27 g, 0.79 mmole) and 3-(1,2,3,6-tetrahydro-4-pyridinyl)-1H-pyrrolo-[2,3-b]pyridine (0.17 g, 0.87 mmole) were dissolved in DMSO (15 mL). Triethylamine (0.22 mL) was added and the reaction mixture heated at 80° C. under nitrogen for 4 hours. The reaction mixture was poured into 400 mL of water and extracted with methylene chloride. The extract was washed with water and 1 N sodium hydroxide solution, dried over $Na_2SO_4$ and filtered. The filtrate was evaporated in vacuum and the residue was chromatographed on silica gel using 10% methanol in methylene chloride as eluant. Upon evaporation of the product fractions in vacuum, 0.22 g (53%) of the (S)-enantiomer of the title compound was obtained as a pale yellow solid, m.p. 207–210° C.

Elemental Analysis for: $C_{22}H_{23}N_3O_3 \cdot 0.6\ H_2O$
Calc'd: C, 68.06; H, 6.28; N, 10.82
Found: C, 68.05; H, 6.06; N, 10.66

EXAMPLE 9

6-Fluoro-3-[1-(8-methoxy-2,3-dihydro-1,4-benzodioxin-2-ylmethyl)-1,2,3,6-tetrahydro-pyridin-4-yl]-1H-indole

[(2R)-8-Methoxy-2,3-dihydro-benzo[1,4]dioxin-2-yl]methyl 4-methylbenzenesulfonate (0.30 g, 0.86 mmole), 6-fluoro-3-(1,2,3,6-tetrahydro-4-pyridinyl)-1H-indole (0.60 g, 2.7 mmole) and sodium bicarbonate (0.80 g) were added to a mixture of dimethylformamide/tetrahydrofuran (1:1 v/v, 20 mL) and the reaction mixture was refluxed under nitrogen for 18 hours. The solvent was evaporated and the residue partitioned between 400 mL each of water and methylene chloride. The layers were separated and the methylene chloride solution was washed with water and saturated aqueous sodium chloride solution, dried over anhydrous potassium carbonate and filtered. The filtrate was evaporated in vacuum and the residue crystallized from chloroform containing 3% methanol, giving 0.23 g (68%) of the (S)-enantiomer of the title compound as an off-white solid, m.p. 184–185° C.

Elemental Analysis for: $C_{23}H_{23}FN_2O_3 \cdot 0.25\ H_2O$.
Calc'd: C, 69.25; H, 5.94; N, 7.02
Found: C, 69.26; N, 5.88; N, 7.10

EXAMPLE 10

3-[4-(1H-Indol-3-yl)-3,6-dihydro-2H-pyridin-1-ylmethyl]-2,3-dihydro-benzo[1,4]dioxine-5-carboxylic Acid Amide (2R)-8-(Aminocarbonyl)-2,3-dihydro-benzo[1,4]dioxin-2-yl]methyl 4-methylbenzenesulfonate (0.60 g, 1.15 mmole) and 3-(1,2,3,6-tetrahydro-4-pyridinyl)-1H-indole (0.68 g, 3.4 mmole) were dissolved in DMSO (6 mL) and the mixture heated at 80° C. under nitrogen for 18 hours. The reaction mixture was poured into water. The mixture was extracted with ethyl acetate and washed with water and saturated aqueous sodium chloride solution, dried over magnesium sulfate and filtered. The filtrate was evaporated under vacuum to give an oil (1.6 g). Chromatography on silica gel using 30% isopropanol in methylene chloride as eluant gave a solid which was recrystallized from methylene chloride to give 0.1 g (15%) of the (S)-enantiomer of the title compounds as a white solid, m.p. 175–178° C.

Elemental Analysis for: $C_{23}H_{23}N_3O_3 \cdot 0.50\ H_2O$
Calc'd: C, 69.33; H, 6.07; N, 10.55
Found: C, 69.40; H, 5.98; N, 10.43

EXAMPLE 11

3-[4-(5-Fluoro-1H-indol-3-yl)-3,6-dihydro-2H-pyridin-1-ylmethyl]-2,3-dihydro-benzo[1,4]dioxine-5-carboxylic Acid Amide (2R)-8-(Aminocarbonyl)-2,3-dihydro-benzo[1,4]dioxin-2-yl]methyl-4-methyl-benzenesulfonate (0.60 g, 1.65 mmole) and 5-fluoro-3-(1,2,3,6-tetrahydro-4-pyridinyl)-1H-indole (0.75 g, 3.4 mmole) were dissolved in DMSO (6 mL) and the mixture heated at 80° C. under nitrogen for 24 hours. The reaction mixture was poured into water, and the product extracted with ethyl acetate. The extract was washed with water and saturated aqueous sodium chloride solution, dried over magnesium sulfate and evaporated in vacuum to give an orange oil (1.0 g). Chromatography on silica gel using 30% isopropanol in methylene chloride as eluant gave the title compound as a solid, which was further purified on another column using 1% methanol in chloroform as eluant. Combination of the product fractions and evaporation in vacuum resulted in the isolation of 0.15 g (23%) of the (S)-enantiomer of the title compound as a yellow solid, m.p. 195–197° C.

Elemental Analysis for: $C_{23}H_{22}FN_3O_3$
Calc'd: C, 67.80; H; 5.44; N, 10.31
Found: C, 67.52; H, 5.66; N, 10.23

EXAMPLE 12

3-(1-{[8-Fluoro-2,3-dihydro-1,4-benzodioxin-2-yl]methyl}-1,2,3,6-tetrahydropyridin-4-yl)-1H-indole

[(2R)-8-Fluoro-2,3-dihydro-benzo[1,4]dioxin-2-ylmethyl 4-methylbenzenesulfonate (1.2 g, 3.5 mmole) was dissolved in a mixture of dimethylformamide/tetrahydrofuran (1:1 v/v, 30 mL) and 3-(1,2,3,6-tetrahydro-4-pyridinyl)-1H-indole (0.60 g, 3.0 mmole) added, followed by the addition of sodium bicarbonate (0.60 g, 7.1 mmole) and the mixture refluxed under nitrogen for 18 hours. The solvent was evaporated in vacuum, and the residue partitioned between 400 mL each of methylene chloride and water. The organic phase was dried over magnesium sulfate and filtered. The filtrate was evaporated and the residue chromatographed on silica gel using 4% methanol in chloroform as eluant. The product fractions were combined and concentrated in vacuum to give 0.20 g (16%) of the (S)-enantiomer of the title compound as a yellow solid, m.p. 174–177° C.

Elemental Analysis for: $C_{22}H_{21}FN_2O_2 \cdot 0.25\ H_2O$
Calc'd: C, 71.62; H, 5.15; N, 7.59
Found: C, 71.69; H, 5.64; N, 7.57

EXAMPLE 13

3-(1-{[7-Methoxy-2,3-dihydro-1,4-benzodioxin-2-yl]methyl}-1,2,3,6-tetrahydropyridin-4-yl)-1H-indole

[(2R)-7-Methoxy-2,3-dihydro-benzo[1,4]dioxin-2-yl]methyl 4-methylbenzenesulfonate (1.5 g, 4.3 mmole) was dissolved in a mixture of dimethylformamide/tetrahydrofuran (1:1 v/v, 30 mL) and 3-(1,2,3,6-tetrahydro-4-pyridinyl)-1H-indole (0.80 g, 4.0 mmole) added, followed by sodium bicarbonate (1.0 g), and the mixture was refluxed under nitrogen for 18 hours. The solvent was removed under vacuum and the residue partitioned between 400 mL each of methylene chloride and water. The layers were separated and the organic phase was washed with water and saturated sodium chloride solution, dried over potassium carbonate and filtered. The filtrate was evaporated to a foam (1.6 g). Chromatography on silica gel using 4% methanol in chloroform as eluant gave 0.20 g of the (S)-enantiomer of the title compound as a yellow solid, m.p. 166–168° C.

Elemental Analysis for: $C_{23}H_{24}N_2O_3 \cdot 0.25\ H_2O$
Calc'd: C, 72.52; H, 6.48; N, 7.35
Found: C, 72.34; H, 5.42; N, 7.14

EXAMPLE 14

5-Fluoro-3-[1-(8-methoxy-2,3-dihydro-benzo[1,4]dioxin-2-ylmethyl)-1,2,3,6-tetrahydro-pyridin-4-yl]-1H-indole

[(2R)-8-Methoxy-2,3-dihydro-benzo[1,4]dioxin-2-yl]methyl 4-methylbenzenesulfonate (0.40 g, 1.1 mmole) was dissolved in a mixture of tetrahydrofuran/dimethylformamide (1:1 v/v, 25 mL) and 5-fluoro-3-(1,2,3,6-tetrahydro-4-pyridinyl)-1H-indole (0.30 g, 1.4 mmole) added, followed by the addition of sodium bicarbonate (0.60 g), and the mixture refluxed for 18 hrs. The solvent was removed under vacuum, and the residue partitioned between 400 mL each of methylene chloride and water. The organic phase was separated, washed with water and saturated aqueous sodium chloride solution, dried over magnesium sulfate and evaporated to a glassy solid (1.0 g). A small portion was converted to the oxalate salt, m.p. 154–156° C.

Elemental Analysis for: $C_{23}H_{23}FN_2O_3 \cdot C_2H_2O_4 \cdot 0.50\ H_2O$

Calc'd: C, 60.85; H, 5.31; N, 5.68

Found: C, 60.39; H, 4.97; N, 5.52

What is claimed is:

1. A compound of formula I

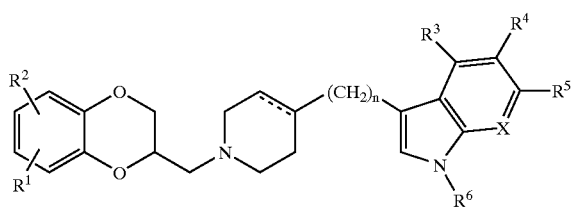

I wherein $R^1$ and $R^2$ are, independently, hydrogen, halogen, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; or $R^1$ and $R^2$, taken together, form methylenedioxy, ethylenedioxy or propylenedioxy;

$R^3$, $R^4$, $R^5$ and $R^7$ are independently selected from hydrogen, halogen, cyano, trifluoromethyl, alkyl of 1 to 6 carbon atoms, alkoxy of 1 to 6 carbon atoms, alkanoyloxy of 2 to 6 carbon atoms;

$R^6$ is hydrogen or alkyl of 1 to 6 carbon atoms;

X is $CR^7$ or N;

A dotted line represents an optional double bond; and n is an integer 0, 1 or 2;

or a pharmaceutically acceptable salt thereof.

2. A compound of claim 1 wherein $R^1$ is hydrogen, halo, cyano, carboxamido, trifluoromethyl, amino, alkyl of one to six carbon atoms or alkoxy of one to six carbon atoms.

3. A compound of claim 1 wherein $R^2$ is hydrogen, halo, cyano, carboxamido, trifluoromethyl, amino, alkyl of one to six carbon atoms or alkoxy of one to six carbon atoms.

4. A compound of claim 1 wherein one of $R^1$ and $R^2$ is hydrogen and the other one of $R^1$ and $R^2$ is hydrogen, amino, alkoxy, halogen, or carboxamido.

5. A compound of claim 4 wherein $R^1$ is alkoxy of one to six carbon atoms and is attached to position 8 of the benzodioxan moiety.

6. A compound of claim 1 wherein $R^3$, $R^4$ and $R^5$ are independently selected from hydrogen, halo, cyano, alkyl of one to six carbon atoms, and alkoxy of one to six carbon atoms.

7. A compound of claim 1 wherein n is 0 or 1.

8. A compound of claim 1 in which $R^1$ and $R^2$ are, independently, hydrogen, halo, cyano, carboxamido, trifluoromethyl, amino, alkyl of one to six carbon atoms or alkoxy of one to six carbon atoms; $R^3$, $R^4$ and $R^5$ are independently selected from hydrogen, halo, cyano, alkyl of one to six carbon atoms, and alkoxy of one to six carbon atoms; n is an integer 0 or 1; or a pharmaceutically acceptable salt thereof.

9. A compound of claim 8 wherein X is $CR^7$ and $R^7$ is hydrogen, halo, cyano, alkyl of one to six carbon atoms, or alkoxy of one to six carbon atoms.

10. A compound of claim 1 in which $R^1$ is alkoxy of one to six carbon atoms and is attached to position 8 of the benzodioxan moiety, $R^2$ and $R^4$ are hydrogen, $R^3$, $R^4$ and $R^5$ are independently selected from hydrogen, halo and cyano, X is $CR^7$, $R^7$ is hydrogen, halo, cyano, n is 0 and the dotted line represents a double bond; or a pharmaceutically acceptable salt thereof.

11. The compound of claim 1 which 5-methoxy-3-[4-[1,2,3,6-tetrahydro-1-[2-(2,3-dihydro[1,4]benzodioxinyl)]methyl]pyridinyl]indole or a pharmaceutically acceptable salt thereof.

12. The compound of claim 1 which is 5-fluoro-3-[4-[1,2,3,6-tetrahydro-1-[2-(2,3-dihydro[1,4]benzodioxinyl)]methyl]pyridinyl]indole or a pharmaceutically acceptable salt thereof.

13. The compound of claim 1 which is 3-[4-(1H-indol-3-yl)-3,6-dihydro-2H-pyridin-1-ylmethyl]-2,3-dihydro-benzo[1,4]dioxin-7-ylamine or a pharmaceutically acceptable salt thereof.

14. The compound of claim 1 which is 2-[4-(1H-indol-3-yl)-3,6-dihydro-2H-pyridin-1-ylmethyl]-2,3-dihydro-benzo[1,4]dioxin-6-ylamine or a pharmaceutically acceptable salt thereof.

15. The compound of claim 1 which 3-[1-(8-methoxy-2,3-dihydro-benzo[1,4]dioxin-2-ylmethyl)-1,2,3,6-tetrahydro-pyridin-4-yl]-1H-indole or a pharmaceutically acceptable salt thereof.

16. The compound of claim 1 which 2-[4-(5-fluoro-1H-indol-3-yl)-3,6-dihydro-2H-pyridin-1-ylmethyl]-2,3-dihydro-benzo[1,4]dioxin-6-ylamine or a pharmaceutically acceptable salt thereof.

17. The compound of claim 1 which 3-[1-(8-methoxy-2,3-dihydro-benzo-[1,4]dioxin-2-ylmethyl)-1,2,3,6-tetrahydro-pyridin-4-yl]-1H-indole-5-carbonitrile or a pharmaceutically acceptable salt thereof.

18. The compound of claim 1 which 3-[1-(8-methoxy-2,3-dihydro-benzo[1,4]-dioxin-2-ylmethyl)-1,2,3,6-tetrahydro-pyridin-4-yl]-1H-pyrrolo[2,3-b]pyridine or a pharmaceutically acceptable salt thereof.

19. The compound of claim 1 which 6-fluoro-3-[1-(8-methoxy-2,3-dihydro-1,4-benzodioxin-2-ylmethyl)-1,2,3,6-tetrahydro-pyridin-4-yl]-1H-indole or a pharmaceutically acceptable salt thereof.

20. The compound of claim 1 which is 3-[4-(1H-indol-3-yl)-3,6-dihydro-2H-pyridin-1-ylmethyl]-2,3-dihydro-benzo[1,4]dioxin-5-carboxylic acid amide or a pharmaceutically acceptable salt thereof.

21. The compound of claim 1 which is 3-[4-(5-fluoro-1H-indol-3-yl)-3,6-dihydro-2H-pyridin-1-ylmethyl]-2,3-dihydro-benzo[1,4]dioxin-5-carboxylic acid amide or a pharmaceutically acceptable salt thereof.

22. The compound of claim 1 which is 3-(1-{[8-fluoro-2,3-dihydro-1,4-benzodioxin-2-yl]methyl}-1,2,3,6-tetrahydropyridin-4-yl)-1H-indole or a pharmaceutically acceptable salt thereof.

23. The compound of claim 1 which is 3-(1-{[7-methoxy-2,3-dihydro-1,4-benzodioxin-2-yl]methyl}-1,2,3,6-tetrahydropyridin-4-yl)-1H-indole or a pharmaceutically acceptable salt thereof.

24. The compound of claim 1 which is 5-fluoro-3-[1-(8-methoxy-2,3-dihydro-benzo[1,4]dioxin-2-ylmethyl)-1,2,3,6-tetrahydro-pyridin-4-yl]-1H-indole or a pharmaceutically acceptable salt thereof.

25. A pharmaceutical composition comprising a compound of the formula I

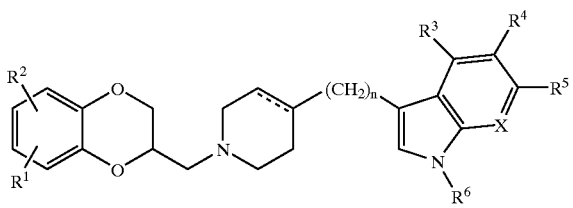

wherein
R¹ and R² are, independently, hydrogen, halogen, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; or R¹ and R², taken together, form methylenedioxy, ethylenedioxy or propylenedioxy;

R³, R⁴, R⁵ and R⁷ are independently selected from hydrogen, halogen, cyano, trifluoromethyl, alkyl of 1 to 6 carbon atoms, alkoxy of 1 to 6 carbon atoms, alkanoyloxy of 2 to 6 carbon atoms;

R⁶ is hydrogen or alkyl of 1 to 6 carbon atoms;

X is CR⁷ or N;

A dotted line represents an optional double bond; and n is an integer 0, 1 or 2;

or a pharmaceutically acceptable salt thereof, and a pharmaceutically acceptable carrier or excipient.

26. A method of treating a subject suffering from a disorder selected from the group consisting of depression, anxiety, panic disorder, obsessive compulsive disorder, social anxiety disorder and generalized anxiety disorder, which comprises providing to the subject suffering from said condition, a therapeutically effective amount of a compound of formula I

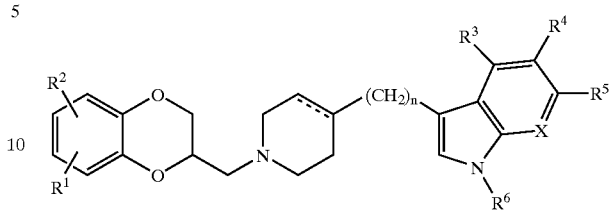

wherein
R¹ and R² are, independently, hydrogen, halogen, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; or R¹ and R², taken together, form methylenedioxy, ethylenedioxy or propylenedioxy;

R³, R⁴, R⁵ and R⁷ are independently selected from hydrogen, halogen, cyano, trifluoromethyl, alkyl of 1 to 6 carbon atoms, alkoxy of 1 to 6 carbon atoms, alkanoyloxy of 2 to 6 carbon atoms;

R⁶ is hydrogen or alkyl of 1 to 6 carbon atoms;

X is CR⁷ or N;

A dotted line represents an optional double bond; and n is an integer 0, 1 or 2;

or a pharmaceutically acceptable salt thereof.

27. The method of claim 26 wherein the condition is depression.

28. The method of claim 26 wherein the condition is obsessive compulsive disorder, panic attacks, generalized anxiety disorder or social anxiety disorder.

29. The method of claim 26 wherein the subject is a human.

* * * * *